United States Patent [19]
Akahane et al.

[11] Patent Number: 5,962,550
[45] Date of Patent: Oct. 5, 1999

[54] DENTAL FILLING RESIN COMPOSITION

[75] Inventors: Shoji Akahane; Hisashi Sato; Hideki Yarimizu; Kazuo Hirota, all of Tokyo, Japan

[73] Assignee: GC Corporation, Tokyo, Japan

[21] Appl. No.: 09/035,264

[22] Filed: Mar. 5, 1998

[30] Foreign Application Priority Data

Mar. 19, 1997 [JP] Japan ..................................... 9-084743

[51] Int. Cl.$^6$ ................................ C08K 3/34; A61K 6/08
[52] U.S. Cl. .......................... 523/116; 523/117; 524/443; 524/450; 524/494; 524/533; 501/69; 501/70; 106/35
[58] Field of Search ..................................... 523/116, 117; 524/443, 450, 494, 533; 501/69, 70; 106/35

[56] References Cited

U.S. PATENT DOCUMENTS

| | | | |
|---|---|---|---|
| 4,342,677 | 8/1982 | Muramatsu et al. | 523/116 |
| 4,433,958 | 2/1984 | Fellmann et al. | 523/116 |
| 4,490,497 | 12/1984 | Evrard et al. | 523/116 |
| 4,524,824 | 6/1985 | Shimokobe et al. | 106/35 |
| 4,591,384 | 5/1986 | Akahane et al. | 106/35 |
| 4,632,824 | 12/1986 | Hirota et al. | 424/49 |
| 4,647,600 | 3/1987 | Kawahara et al. | 523/116 |
| 4,652,593 | 3/1987 | Kawahara et al. | 523/116 |
| 4,678,436 | 7/1987 | Kondo et al. | 433/228.1 |
| 4,775,592 | 10/1988 | Akahane et al. | 501/55 |
| 4,900,697 | 2/1990 | Akahane et al. | 501/57 |
| 5,063,257 | 11/1991 | Akahane et al. | 523/116 |
| 5,453,456 | 9/1995 | Mitra et al. | 523/116 |

*Primary Examiner*—Andrew E. C. Merriam
*Attorney, Agent, or Firm*—Oblon, Spivak, McClelland, Maier & Neustadt, P.C.

[57] ABSTRACT

A dental filling resin composition is disclosed, comprising: a reaction product between an aluminosilicate glass powder containing at least one element selected from Ca, Sr, and Ra and an organic acid containing one or more carboxyl groups in one molecule thereof, a methanol-insoluble polymer, a monomer containing at least one unsaturated double bond and having no acidic group, and a polymerization initiator, and optionally a filler.

The dental filling resin composition of the invention has not only superior mechanical characteristics and esthetics but also an ability to release a fluorine ion and therefore, can be suitably used for a wide variety of clinical applications such as filling restoration of tooth, core construction, or sealing of pit and fissure.

13 Claims, No Drawings

DENTAL FILLING RESIN COMPOSITION

FIELD OF THE INVENTION

The present invention relates to a dental filling resin composition which is mainly used for filling restoration of tooth, core construction, sealing of pit and fissure, and the like.

BACKGROUND OF THE INVENTION

Hitherto, dental composite resins or dental glass ionomer cements have been used for filling restoration of fine deficient portions of tooth, core construction after the toot canal treatment, and the like. Also, materials having a great fluidity imparted to dental composite resins or dental glass ionomer cements, which are called as a dental sealant, have been used for sealing of pit and fissure for the purpose of preventing a tooth from occurrence of dental caries.

The dental composite resins have such features that they have relatively high mechanical characteristics and that they have a color tone close to a tooth and are particularly suitable for filling restoration or core construction.

On the other hand, although the dental glass ionomer cements are inferior to the dental composite resins with respect to the mechanical characteristics and esthetics such as color tone or surface smoothness, they have such a feature that they release a fluorine ion. The released fluorine ion replaces a hydroxyl group in an apatite in the dental structure to increase the acid resistance of the apatite, leading to prevention of dental caries from occurrence or making it hard to disease secondary caries. Accordingly, the dental glass ionomer cements are particularly suitable for filling restoration or sealing of pit and fissure.

In recent years, the development of materials having features of both dental composite resin and a dental glass ionomer cement in combination is being achieved. For example, resin-reinforced glass ionomer cements are ones comprising a dental glass ionomer cement having unsaturated double bond-containing monomer compounded therewith. However, the resin-reinforced glass ionomer cements have not enough mechanical characteristics compared with the dental composite resins. Also, in order to provide the dental composite resin with an ability for releasing a fluorine ion, a product comprising a dental composite resin having a quaternary ammonium salt of hydrofluoric acid compounded therewith, which is called as a compomer composite, is known. However, the stability of this material in an oral cavity is low due to the compounding of a quaternary ammonium salt of hydrofluoric acid. Accordingly, it can not be said yet that the development of materials having respective features of a dental composite resin and of a dental glass ionomer cement in combination is sufficient, and the materials having clinically satisfactory properties have not been developed yet.

SUMMARY OF THE INVENTION

Under such circumstances, an object of the present invention is to provide a dental filling resin composition having superior mechanical characteristics and esthetics as in a dental composite resin and also having an ability for releasing a fluorine ion as in a dental glass ionomer cement in combination and being able to be suitably used in a wide variety of clinical applications such as filling restoration of tooth, core construction, or sealing of pit and fissure.

In order to achieve the above-described object, the present inventors made extensive and intensive investigations. As a result, it has been found that when a reaction product between an aluminosilicate glass powder containing at least one element selected from Ca, Sr, and Ra and an organic acid containing one or more carboxyl groups in one molecule thereof is contained in a dental filling resin composition comprising, as a basic component, a dental composite resin having superior mechanical characteristics and esthetics, not only an ability for effectively releasing a fluorine ion can be imparted, but also the superior mechanical characteristics and esthetics can be kept, leading to accomplishment of the present invention.

That is, the dental filling resin composition according to the present invention comprises:

(A) a reaction product between an aluminosilicate glass powder containing at least one element selected from Ca, Sr, and Ra and an organic acid containing one or more carboxyl groups in one molecule thereof, (B) a methanol-insoluble polymer, (C) a monomer containing at least one unsaturated double bond and having no acidic group, and (D) a polymerization initiator, and optionally (E) a filler which is added, if necessary

DETAILED DESCRIPTION OF THE INVENTION

The dental filling resin composition according to the present invention will be described below in detail with reference to each of the constituting components.

The reaction product between an aluminosilicate glass powder containing at least one element selected from Ca, Sr, and Ra and an organic acid containing one or more carboxyl groups in one molecule thereof is the most characteristic component in the present invention and plays a role for imparting an ability to release a fluorine ion to the dental filling resin composition according to the present invention.

In the reaction product, the aluminosilicate glass powder containing at least one element selected from Ca, Sr, and Ra is an aluminosilicate glass powder capable of releasing a fluorine ion, and specifically, the fluoroaluminosilicate glass powder comprising from 20 to 50% by weight of $SiO_2$, from 20 to 40% by weight of $Al_2O_3$, from 15 to 40% by weight of SrO, from 1 to 20% by weight of $F_2$, and from 0 to 15% by weight of $P_2O_5$ in terms of reduced amounts and not substantially containing not only alkali metal elements such as Li, Na, K, Rb, or Cs but also Be, Mg, or Ba as an alkaline earth metal elements as described in Published Japanese Patent Application No. 55882/1995 can be suitably used. Incidentally, this glass powder has also an advantage such that it can meaningfully give X-ray contrast properties necessary from the viewpoint of dental clinics. Also, this glass powder can contain a lanthanide metal element such as La, Gd, or Yb, if desired. When this glass powder is contained in the dental filling resin composition as a reaction product with an organic acid containing one or more carboxyl groups in one molecule thereof, it exhibits an ability to release a fluorine ion. However, in case where this glass powder is singly contained, it has such a feature that the amount of a released fluorine ion is very low.

Examples of the organic acid containing one or more carboxyl groups in one molecule thereof which can be used in the present invention include L-aspartic acid, L-arginine, citric acid, glycine, glycolic acid, DL-glyceric acid, gluconic acid, glucuronic acid, glutaric acid, acetonedicarboxylic acid, tartaric acid, cyclopentanetetracarboxylic acid, diglycolic acid, diethylmalonic acid, L-cysteic acid, oxalic acid, sulfosalicylic acid, tartronic acid, tricarballylic acid, tetrahydrofurantetracarboxylic acid, meso-butane-1,2,3,4-tetracarboxylic acid, trimellitic acid, lactic acid, benzenepentacarboxylic acid, malonic acid, DL-mandelic acid, benzenehexacarboxylic acid, and malic acid. These organic acids can be used alone or in admixture of two or more thereof. A suitable amount of the organic acid which can be contained in the reaction product is from 0.1 to 45% by weight. In case where the amount of the organic acid is less than 0.1% by weight, the amount of a fluorine ion released from the reaction product is small, whereas in case where the amount of the organic acid exceeds 45% by weight, the liberated organic acid causes a reduction in the pH of the dental filling resin composition, or the reaction product tends to be coagulated during the preparation. Incidentally, though polymers such as polyacrylic acids could be used as the organic acid, in this case, there may be caused the retention of carboxyl groups or the retention of water in a cured material, leading to a decrease in the mechanical properties.

The preparation of the reaction product can be carried out in, for example, a method in which an aluminosilicate glass powder containing at least one element selected from Ca, Sr, and Ra is mixed with a volatile organic solvent such as methanol, ethanol, or t-butanol to form a slurry. Then the slurry is mixed and reacted with an aqueous solution of an organic acid containing one or more carboxyl groups in one molecule thereof, and the reaction mixture is subjected to aging in the vicinity of room temperature, followed by drying upon heating at approximately 120° C.

Incidentally, since the particle size of the glass powder influences the particle size of the reaction product, when the dental filling resin composition is applied to filling restoration of tooth, it is preferred to use a fine glass powder having a maximum particle diameter of smaller than 10 $\mu$m and a mean particle diameter of smaller than 5 $\mu$m and particularly, a glass powder having a particle diameter of from 0.05 to 8 $\mu$m and a mean particle diameter of from 0.1 to 2.0 $\mu$m from the standpoints of esthetics such as smoothness of a cured material. However, when the glass powder is used for core construction or sealing of pit and fissure, even glass powders having a larger particle size can be used, and those having a maximum particle diameter of smaller than 50 $\mu$m can be used.

Such a reaction product has an effect for imparting an ability to release a fluorine ion to the resin. A suitable amount of the reaction product which can be contained in the dental filling resin composition according to the present invention is from 5 to 85% by weight. When the amount of the reaction product is less than 5% by weight, the amount of a released fluorine ion is little, whereas when the amount of the reaction product exceeds 85% by weight, the clinical workability tends to be lowered.

Incidentally, the reaction product between an aluminosilicate glass powder containing at least one element selected from Ca, Sr, and Ra and an organic acid containing one or more carboxyl groups in one molecule thereof can be compounded in the dental filling resin composition according to the present invention after being previously modified with an alkoxy compound. Examples of the alkoxy compound which can be used for the modification in the present invention include alkoxysilanes containing an unsaturated double bonds such as 3-methacryloxypropyl trimethoxysilane, 3-methacryloxypropyl triethoxysilane, 3-acryloxypropyl trimethoxysilane, 3-methacryloxypropylmethyl dimethoxysilane, 3-methacryloxypropylmethyl diethoxysilane, 3-acryloxypropylmethyl dimethoxysilane, 2-methacryloxyethoxypropyl trimethoxysilane, vinyl trimethoxysilane, vinyl triethoxysilane, or vinyl tris(2-methoxyethoxy)silane; alkoxysilanes containing a glycidoxy group such as 2-(3,4-epoxycyclohexyl)ethyl trimethoxysilane, 3-glycidoxypropyl trimethoxysilane, 3-glycidoxypropylmethyl dimethoxysilane, 3-glycidoxypropylmethyl diethoxysilane, or 3-glycidoxypropyl triethoxysilane; alkoxysilanes containing an amino group such as N-2-(aminoethy)-3-aminopropyl trimethoxysilane, N-2-(aminoethyl)-3-aminopropyl triethoxysilane, 3-aminopropyl trimethoxysilane, 3-aminopropyl triethoxysilane, or N-phenyl-3-aminopropyl trimethoxysilane; and alkoxysilanes containing a mercapto group such as 3-mercaptopropyl trimethoxysilane or 3-mercaptopropyl triethoxysilane. Examples of titanate coupling agents containing an unsaturated double bond which can be used in the present invention include isopropyl dimethacryl isostearoyl titanate, isopropyl diacryl isostearoyl titanate, isopropyl trimethacryl titanate, isopropyl triacryl titanate, oxyacetyl dimethacryl titanate, and oxyacetyl diacryl titanate. Examples of titanate coupling agents containing an amino group which can be used in the present invention include isopropyl tri(N-diethylamino)titanate, isopropyl tri(2-aminobenzoyl)titanate, isopropyl tri(tetraethylenetriamine)titanate, isopropyl 4-aminobenzenesulfonyl di(dodecylbenzenesulfonyl) titanate, and isopropyl di(4-aminobenzoyl)isostearoyl titanate. They are selected depending upon the monomer to be complexed, and in particular, alkoxy compounds containing an unsaturated double bond are used alone or in admixture, if desired. Besides the above-enumerated compounds, compounds containing no functional group other than an alkoxy group, such as methyl trimethoxysilane, dimethyl dimethoxysilane, phenyl trimethoxysilane, diphenyl dimethoxysilane, methyl triethoxysilane, dimethyl diethoxysilane, phenyl triethoxysilane, diphenyl dimethoxysilane, isobutyl trimethoxysilane, decyl trimethoxysilane, tetraethoxysilane, or tetramethoxysilane, can also be used.

These alkoxy compounds modify the reaction product and mitigate a difference in refractive index between the matrix resin and the reaction product, thereby exhibiting such effects to impart a proper semi-transparency to the cured material and also to make the mechanical characteristics stable. Incidentally, the alkoxy compound is usually used in an amount of from 0.1 to 100 parts by weight based on 100 parts by weight of the reaction product.

The methanol-insoluble polymer, the monomer containing at least one unsaturated double bond and having no acidic group, the polymerization initiator, the filler to be added, if desired, and the like are each a component to constitute a resin material generally used in the dentistry. Of these, the methanol-insoluble polymer has an effect to impart good workability to the resin, and specific examples thereof include pearl polymerization powder such as polymethyl methacrylate, 2-hydroxyethyl methacrylate-methyl methacrylate copolymer, styrene-maleic anhydride copolymer, acrylic polymer, or acrylic acid-maleic acid copolymer, ground powder of bulk polymer, and powder of emulsion polymer. These compounds can be used alone or in admixture of two or more thereof. A suitable amount of the methanol-insoluble polymer which can be used in the present invention is from 0.1 to 20% by weight in the dental filling resin composition. If the amount of the methanol-insoluble polymer is less than 0.1% by weight, good workability is not attained, whereas if it exceeds 20% by weight, the mechanical properties are liable to be lowered.

The monomer containing at least one unsaturated double bond and having no acidic group forms the resin matrix, and monomers or resins containing at least one unsaturated double bond such as unsaturated polyesters are usually used for such monomers. Specific examples thereof include methyl methacrylate, ethyl methacrylate, isopropyl methacrylate, 2-hydroxyethyl methacrylate, 3-hydroxypropyl methacrylate, 2-hydroxypropyl methacrylate, 2-hydroxy-1,3-dimethacryloxypropane, n-butyl methacrylate, isobutyl methacrylate, tetrahydrofurfuryl methacrylate, glycidyl methacrylate, 2-methoxyethyl methacrylate, 2-ethylhexyl methacrylate, benzyl methacrylate, phenyl methacrylate, phenoxyethyl methacrylate, 2,2-bis(methacryloxyphenyl)propane, 2,2-bis[4-(2-hydroxy-3-methacryloxypropoxy)phenyl]propane, 2,2-bis(4-methacryloxydiethoxyphenyl)propane, 2,2-bis(4-methacryloxypolyethoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritol tetramethacrylate, and acrylates corresponding to these methacrylates. Also, methacrylates or acrylates containing urethane bond in a molecule thereof, specifically di-2-methacryloxyethyl-2,2,4-trimethylhexamethylene dicarbamate and acrylates corresponding thereto, can be enumerated. These methacrylates or acrylates can be used alone or in admixture of two or more thereof.

As the polymerization initiator, a photopolymerization initiator which causes a polymerization reaction upon irradiation with a light or a chemical polymerization initiator which causes a polymerization reaction by a redox reaction or the like can be used.

As the photopolymerization initiator, a combination of a sensitizer and a reducing agent can be used. Examples of the sensitizer which can be used in the present invention include camphorquinone, benzil, diacetyl, benzyl dimethyl ketal, benzyl diethyl ketal, benzyl di(2-methoxyethyl)ketal, 4,4"-dimethylbenzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethylthioxanthone, thioxanthone-10,10-dioxide, thioxanthone-10-oxide, benzoin methyl ether, benzoin ethyl ether, isopropyl ether, benzoin isobutyl ether, benzophenone, bis(4-dimethylaminophenyl)ketone, 4,4'-bisdiethylaminobenzophenone, acylphosphine oxides such as (2,4,6-trimethylbenzoyl)diphenylphosphine oxide, and azide group-containing compounds. These compounds can be used alone or in admixture of two or more thereof.

As the reducing agent, tertiary amines and the like can be used. Suitable examples of tertiary amines which can be used in the present invention include N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. Besides, benzoyl peroxide, sodium sulfinate derivatives, or organometallic compounds can also be used as the reducing agent.

A photopolymerization type dental filling resin composition obtained by compounding such a photopolymerization initiator can achieve the polymerization reaction upon irradiation with actinic light rays such as ultraviolet light rays or visible light rays. Examples of light sources which can be used in the present invention include a variety of mercury lamps such as ultra high, high, intermediate and low pressure ones, chemical lamp, carbon arc lamps, metal halide lamps, fluorescent lamps, tungsten lamps, xenon lamps, and argon ion lasers.

Also, examples of the chemical polymerization initiators which can be used in the present invention include a combination of benzoyl peroxide and a tertiary amine, a combination of benzoyl peroxide and N-phenylglycine, a combination of benzoyl peroxide and sodium p-toluenesulfinate, a combination of benzoyl peroxide and sodium benzenesulfinate, a combination of benzoyl peroxide, sodium p-toluenesulfinate or sodium benzenesulfinate and an aromatic tertiary amine, a combination of potassium peroxosulfate and an aromatic tertiary amine, and a combination of sodium peroxosulfate and an aromatic tertiary amine.

In addition, if desired, the filler can be contained in the dental filling resin composition according to the present invention. Examples of the filler which can be used in the present invention include colloidal silica, barium glass powder and aluminosilicate glass powder containing at least one element selected from Ca, Sr, and Ra. The filler is used for the purpose for imparting mechanical properties or viscosity suitable for various applications of the dental filling resin composition. These compounds can be used alone or in admixture of two or more thereof. Incidentally, when the filler is a barium glass powder or an aluminosilicate glass powder, it can be modified with the alkoxy compound as described above as in the case of the reaction product. While the alkoxy compound is properly selected and used depending on the monomer to be complexed, in general, alkoxy compounds containing at least one unsaturated double bond are suitably used.

EXAMPLES

The present invention is hereunder described in more detail with reference to the following Examples, but it should not be construed that the invention is limited thereto. With respect to each of the Examples and Comparison Examples shown in Table 1 below, the bending strength, the surface roughness, the amount of released fluorine ion, and the pH were measured, respectively.

Preparation of Glass Powder

G1 Powder

Based on the description of Example 2 of Published Japanese Patent Application No. 55882/1995, 34.0 g of kaolin ($Al_2O_3 \cdot 2SiO_2 \cdot 2H_2O$), 25.8 g of strontium carbonate ($SrCO_3$), 15.6 g of aluminum phosphate ($AlPO_4$), 13.3 g of aluminum fluoride ($AlF_3$), and 11.3 g of silica sand ($SiO_2$) were each weighed and thoroughly mixed, and the mixture was then melted in a platinum crucible while keeping at 1,250° C. for 3 hours, followed by quenching and grinding to prepare a glass powder having a maximum particle size of 45 μm and a mean particle size of 12.2 μm.

G2 Powder

Based on the description of Example 4 of the above-cited Japanese Patent Publication Gazette, 45.4 g of kaolin ($Al_2O_3 \cdot 2SiO_2 \cdot 2H_2O$), 8.1 g of silica sand ($SiO_2$), 20.2 g of strontium carbonate ($SrCO_3$), 8.8 g of calcium fluoride ($CaF_2$), 6.8 g of aluminum fluoride ($AlF_3$), and 10.7 g of potassium hydrogenphosphate ($CaHPO_4 \cdot 2H_2O$) were each weighed and thoroughly mixed, and the mixture was then melted in a ceramic crucible while keeping at 1,150° C. for 5 hours, followed by quenching and grinding to prepare a glass powder having a maximum particle size of 5 μm and a mean particle size of 1.1 μm.

Preparation of Reaction Product

Each of the above-described glass powders (G1 and G2) was suspended in ethanol to form a slurry, which was then added dropwise and mixed with an aqueous solution of an organic acid as shown in Table 1 below. The mixture was aged at room temperature for 12 hours and dried at 120° C. to prepare a reaction product.

Modification with Alkoxy Compound

Each of the reaction products was suspend in an alcohol to form a slurry, which was then added successively with an alkoxy compound as shown in Table 1 below and with an acetic acid aqueous solution having a pH of from 3 to 4. After keeping for several hours, the resulting slurry was passed through a heating pipe and sprayed into an atmosphere under reduced pressure, thereby modifying its surface. When the alkoxy compound had no organic substituent other than the alkoxy group, the obtained powder was gradually heated to 400° C. at maximum, and its surface was then modified with an alkoxy compound having an organic functional group. When the reaction product with the organic acid was modified with the alkoxy compound, the drying was carried out at a temperature of 150° C. or below. Incidentally, the modification of the glass powder used as the filler with the alkoxy compound was carried out in a similar manner.

Preparation of Dental Filling Resin Composition

The compounding ratios of the reaction product, the polymer, the monomer, and the filler in each of the Examples and Comparison Examples are shown in Table 1 below. 100 parts by weight of these components in total were added and mixed with each of 0.2 part by weight of camphorquinone and 1.0 part by weight of N,N-dimethylaminoethyl methacrylate as the photopolymerization initiator to prepare a photopolymerization type dental filling resin composition.

Comparison tests with respect to the dental filling resin compositions of the respective Examples and Comparison Examples were carried out in the following manners. The test results were summarized and shown in Table 1 below.

Bending Strength

Each of the compositions of the Examples and Comparison Examples was charged in a mold having a size of 2 mm×2 mm×25 mm, press adapted onto a glass sheet via a cellophane, and then cured upon irradiation with a light for 60 seconds by means of a visible light ray irradiator (a product name: New Light VL-II, manufactured by GC Corporation) from above and on one side thereof. The obtained specimen was dipped in distilled water at 37° C. for 24 hours and subjected to a three-point bending test by means of a bending tester (a product name: Autograph, manufactured by Shimadzu Corporation) with a span of 20 mm at a crosshead speed of 1 mm/min.

Surface Roughness

Each of the compositions of the Examples and Comparison Examples was charged in a mold having a size of 15 mm×15 mm×2 mm, press adapted onto a glass sheet via a cellophane, and then cured upon irradiation with a light for 60 seconds by means of a visible light ray irradiator (a product name: New Light VL-II, manufactured by GC Corporation) from above and on one side. Subsequently, the irradiated surface was polished with an emery paper #600 and then abraded successively with a water paste of polishing sand (fine) for the prosthodontics and a water paste of alumina (0.3 μm) for finishing. The surface roughness of the finished abraded surface was measured by means of a surface roughness tester (manufactured by Kosaka Kenkyusho K.K.) in terms of the 10-point mean roughness.

Amount of Released Fluorine Ion

A mold prepared by adhering an acrylic resin ring having a diameter of 6 mm and a height of 1 mm to an acrylic resin sheet, thereby controlling its exposed area was charged with each of the compositions of the Examples and Comparison Examples and cured by means of a visible light ray irradiator (a product name: New Light VL-II, manufactured by GC Corporation). The thus obtained specimen was dipped in distilled water (8 ml, 37° C.) and measured for the fluorine ion strength by means of fluorine ion measurement equipment (a product name: IM-40S, manufactured by Toa Denpa Kogyo K.K.). Table 1 shows the values obtained 7 days after the start of the dipping.

Measurement of pH

A mold prepared by adhering an acrylic resin ring having a diameter of 6 mm and a height of 1 mm to an acrylic resin sheet, thereby controlling its exposed area was charged with each of the compositions of the Examples and Comparison Examples and cured by means of a visible light ray irradiator (a product name: New Light VL-II, manufactured by GC Corporation). The thus obtained specimen was dipped in distilled water (8 ml, 37° C.) and measured for the hydrogen ion strength by means of a hydrogen ion measurement equipment (a product name: F-23, manufactured by Horiba, Ltd.), whereby the acid strength was defined to be an index. Table 1 shows the values obtained 7 days after the start of the dipping. Incidentally, the used distilled water had a pH of 6.3.

TABLE 1

| | Reaction Product (weight %) [Glass powder (parts by weight)/Organic Acid/Alkoxy Compound] | Polymer (weight %) | Filler (weight %) [Kind of Filler (parts by weight)] | Monomer (weight %) [Kind of Monomer (parts by weight)] | Bending Strength (MPa) | Surface Roughness (μm) | Fluorine Ion (μg/cm²) | pH | Remarks |
|---|---|---|---|---|---|---|---|---|---|
| Example 1 | 73 [G2: 76/Tart: 24/ TEOS: 3; 3-MPTMS: 2] | 2 [PMMA] | 1 [Colloidal Silica] | 24 [Bis-MEPP: 40; UDMA: 20; 2-HEMA: 20] | 145 | 0.2 | 121 | 5.9 | Good as a filling restorative |
| Example 2 | 75 [G2: 86/TTR: 14/ TEOS: 3; 3-MPTMS: 2] | 1.5 [PMMA] | 0.5 [Colloidal Silica] | 23 [Bis-MEPP: 30; GMA: 20; UDMA: 20; 2-HEMA: 10] | 155 | 0.3 | 89 | 5.7 | Good as a filling restorative |
| Example 3 | 71 [G2: 75/THFTC: 25/ TEOS: 3; 3-MPTMS: 2] | 3 [PEMA] | 3 [Colloidal Silica] | 23 [Bis-2OHMPOPP: 62; TEGDMA: 38] | 144 | 0.3 | 111 | 6.1 | Good as a filling restorative |
| Example 4 | 74 [G2: 88/BzC6: 12/ TEOS: 2; 3-MPTMS: 2] | 1 [PEMA] | 3 [Colloidal Silica] | 22 [Bis-MEPP: 80; 2-HPMA: 20] | 154 | 0.2 | 93 | 6.0 | Good as a filling restorative |
| Example 5 | 74 [G2: 98/Citr: 2/TEOS: 2; 3-MPTMS: 2] | 1 [PMMA] | 3 [Colloidal Silica] | 22 [Bis-MEPP: 30; UDMA: 40; 3-HPMA: 30] | 159 | 0.2 | 33 | 5.9 | Good as a filling restorative |
| Example 6 | 71 [G2: 94/TCAR: 6/3-MPTMS: 4] | 3 [PMMA] | 2 [Colloidal Silica] | 24 [Bis-MEPP: 40; UDMA: 40; 2-HPMA: 30] | 133 | 0.2 | 42 | 5.8 | Good as a filling restorative |
| Example 7 | 78.1 [G2: 76/Tart: 22; L-As: 2/TEOS: 3; 3-MPTMS: 2] | 0.1 [PMMA] | 0.2 [Colloidal Silica] | 21.6 [Bis-MEPP: 40; UDMA: 20; 2-HEMA: 20] | 146 | 0.3 | 122 | 5.7 | Good as a filling restorative |
| Example 8 | 72.6 [G2: 86/TTR: 12; L-Ag: 2/TEOS: 2; 3-MPTMS: 0.2] | 4 [PMEA] | 0.4 [Colloidal Silica] | 23 [Bis-MEPP: 20; UDMA: 50; 2-HEMA: 30] | 122 | 0.2 | 72 | 5.9 | Good as a filling restorative |
| Example 9 | 71.7 [G2: 76/THFTC: 18; GN: 6/TEOS: 3; 3-MPTMS: 2] | 6 [PEMA] | 0.5 [Colloidal Silica] | 21.8 [Bis-2OHMPOPP: 62; TEGDMA: 38] | 125 | 0.2 | 77 | 5.2 | Good as a filling restorative |
| Example 10 | 74.8 [G2: 95/BzC6: 4; GOL: 1/3-MPTMS: 4] | 1 [PMMA] | 0.2 [Colloidal Silica] | 24 [Bis-MEPP: 40; UDMA: 20; 2-HEMA: 20] | 151 | 0.3 | 39 | 5.6 | Good as a filling restorative |
| Example 11 | 77.1 [G2: 90/Tart: 8; DL-G: 2/TEOS: 3; 3-MPTMS: 2] | 0.5 [PMMA] | 0.8 [Colloidal Silica] | 21.6 [Bis-MEPP: 40; UDMA: 20; 2-HEMA: 20] | 143 | 0.2 | 55 | 5.2 | Good as a filling restorative |
| Example 12 | 74.3 [G2: 86/TTR: 8; GLC: 2/3-MPTMS: 4; 3-APTMS: 0.2] | 2.7 [PMMA] | 0.2 [Colloidal Silica] | 22.8 [Bis-MEPP: 45; UDMA: 45; 2-HEMA: 10] | 136 | 0.3 | 68 | 6.1 | Good as a filling restorative |
| Example 13 | 70.4 [G2: 90/THFTC: 6; GlcUA: 4/TEOS: 3; 3-MPTMS: 2] | 6 [PEMA] | 1.8 [Colloidal Silica] | 21.8 [Bis-2OHMPOPP: 62; TEGDMA: 38] | 133 | 0.2 | 45 | 6.0 | Good as a filling restorative |
| Example 14 | 72 [G2: 94/BzC6: 5; GLT: 1/ TEOS: 3; 3-MPTMS: 2] | 3.8 [PMMA] | 0.2 [Colloidal Silica] | 24 [Bis-MEPP: 40; UDMA: 20; 2-HEMA: 20] | 123 | 0.3 | 39 | 6.1 | Good as a filling restorative |
| Example 15 | 74.1 [G2: 90/Tart: 8; AdC: 2/TEOS: 3; 3-MPTMS: 2] | 1.2 [PMMA] | 0.2 [Colloidal Silica] | 24.5 [Bis-MEPP: 40; UDMA: 20; 2-HEMA: 20] | 121 | 0.2 | 40 | 5.6 | Good as a filling restorative |
| Example 16 | 76 [G2: 90/TTR: 8; cptC: 2/ | 0.8 | 0.2 | 23 [Bis-MEPP: 45; | 120 | 0.2 | 55 | 5.7 | Good as a |

TABLE 1-continued

| | Reaction Product (weight %) [Glass powder (parts by weight)/Organic Acid/Alkoxy Compound] | Polymer (weight %) | Filler (weight %) [Kind of Filler (parts by weight)] | Monomer (weight %) [Kind of Monomer (parts by weight)] | Bending Strength (MPa) | Surface Roughness (μm) | Fluorine Ion (μg/cm²) | pH | Remarks |
|---|---|---|---|---|---|---|---|---|---|
| Example 17 | 3-MPTMS: 2; 3-APTMS: 0.2] | [PMMA] | [Colloidal Silica] | UDMA: 45; 2-HEMA: 10] | 126 | 0.2 | 53 | 5.7 | Good as a filling restorative |
| Example 18 | 77.1 [G2: 76/THFTC: 4; dGL: 1/TEOS: 0.2; 3-MPTMS:4] | 0.8 [PEMA] | 0.3 [Colloidal Silica] | 21.8 [Bis-2OHMPOPP: 62; TEGDMA: 38] | 120 | 0.2 | 61 | 5.9 | Good as a filling restorative |
| Example 19 | 68 [G2: 76/BzC6: 10; dEtM: 6/TEOS: 3; 3-MPTMS: 2] | 8.8 [PEMA] | 0.2 [Colloidal Silica] | 23 [Bis-MEPP: 40; UDMA: 20; 2-HEMA: 20] | 141 | 0.2 | 33 | 6.1 | Good as a filling restorative |
| Example 20 | 64 [G2: 94/Tart: 4; L-Cys: 2/TEOS: 0.5; 3-MPTMS: 6] | 1 [PMMA] | 12 [G2: 100; 3-MPTMS: 2] | 23 [Bis-MEPP: 40; UDMA: 20; 2-HEMA: 20] | 122 | 0.2 | 38 | 6.1 | Good as a filling restorative |
| Example 21 | 73 [G2: 95/TTR: 4; Ox: 1/3-MPTMS: 2; 3-APTMS: 0.2] | 3.8 [PMMA] | 0.2 [Colloidal Silica] | 23 [Bis-MEEP: 45; UDMA: 45; 2-HEMA: 10] | 120 | 0.3 | 40 | 5.8 | Good as a filling restorative |
| Example 22 | 72 [G2: 88/THFTC: 10; SuSA: 2/TEOS: 5; 3-MPTMS: 2] | 1.8 [PEMA] | 0.6 [Colloidal Silica] | 25.6 [Bis-2OHMPOPP: 62; TEGDMA: 38] | 131 | 0.2 | 31 | 6.2 | Good as a filling restorative |
| Example 23 | 55 [G2: 94/BzC6: 4; mBTC: 2/3-MPTMS: 4] | 4 [PMMA] | 17 [G2: 100; 3-MPTMS: 6] | 24 [Bis-MEPP: 40; UDMA: 20; 2-HEMA: 20] | 149 | 6.8 | 34 | 5.7 | Good for core contruction |
| Example 24 | 33 [G1: 76/Tart: 20; TMRt: 4/TEOS: 10; 3-MPTMS: 4] | 1 [PMMA] | 44.6 [G2: 100; 3-MPTMS: 6] | 21.4 [Bis-MEPP: 40; UDMA: 20; 2-HEMA: 20] | 131 | 0.3 | 57 | 5.8 | Good as a filling restorative |
| Example 25 | 76.4 [G2: 86/THFTC: 8; Lac: 6/3-MPTMS: 2; 3-APTMS: 0.2] | 0.5 [PMMA] | 8.5 [G2: 100; 3-MPTMS: 6] | 23.1 [Bis-MEPP: 45; UDMA: 45; 2-HEMA: 10] | 121 | 0.4 | 73 | 5.7 | Good as a filling restorative |
| Example 26 | 66.4 [G2: 80/THFTC: 18; MLN: 2/TEOS: 3; 3-MPTMS: 2] | 2.3 [PEMA] | 12.2 [G2: 100; 3-MPTMS: 6] | 22.8 [Bis-2OHMPOPP: 62; TEGDMA: 38] | 151 | 0.3 | 35 | 5.9 | Good as a filling restorative |
| Example 27 | 66.2 [G2: 92/BzC6: 7; DL-M: 1/TEOS: 3; 3-MPTMS: 2] | 0.4 [PMMA] | | 21.2 [Bis-MEPP: 40; UDMA: 20; 2-HEMA: 20] | 140 | 6.7 | 41 | 5.7 | Good for core construction |
| Example 28 | 71.1 [G1: 90/Tart: 8; Mal: 2/3-MPTMS: 2; 3-APTMS: 0.2] | 10 [PSnMA] | 0.2 [Colloidal Silica] | 18.9 [Bis-MEPP: 45; UDMA: 45; BG: 10] | 143 | 0.3 | 131 | 5.5 | Good as a filling restorative |
| Example 29 | 76 [G2: 57/Tart: 30; TTR: 3; THFTC: 10/TEOS: 10; 3-MPTMS: 4] | 0.6 [PEMA] | 0.2 [Colloidal Silica] | 23.2 [Bis-2OHMPOPP: 62; TEGDMA: 38] | 136 | 0.3 | 112 | 6.1 | Good as a filling restorative |
| Example 30 | 72 [G2: 76/Tart: 10; THFTC: 4; BzC6: 6/TEOS: 3; 3-MPTMS: 2] | 3.8 [PMMA] | 0.2 [Colloidal Silica] | 24 [Bis-MEPP: 40; UDMA: 20; 2-OHDMP: 20] | 140 | 0.2 | 21 | 6.1 | Good as a filling restorative |
| Example 31 | 76 [G2: 99.9/Tart: 0.1/3-MPTMS: 2.0] | 0.8 [PEMA] | 0.2 [Colloidal Silica] | 23 [Bis-2OHMPOPP: 62; TEGDMA: 38] | 121 | 0.2 | 34 | 6.0 | Good as a filling restorative |
| | 77.2 [G2: 96/Tart: 4/3-MPTMS: 2] | 0.1 [PEMA] | | 22.5 [Bis-2OHMPOPP: 62; TEGDMA: 38] | | | | | |

TABLE 1-continued

| | Reaction Product (weight %) [Glass powder (parts by weight)/Organic Acid/Alkoxy Compound] | Polymer (weight %) | Filler (weight %) [Kind of Filler (parts by weight)] | Monomer (weight %) [Kind of Monomer (parts by weight)] | Bending Strength (MPa) | Surface Roughness (μm) | Fluorine Ion (μg/cm²) | pH | Remarks |
|---|---|---|---|---|---|---|---|---|---|
| Example 32 | 56.2 [G1: 96/Tart: 4/ TEOS: 5; 3-MPTMS: 3] 28.4 [G2: 96/Tart: 4/ TEOS: 5; 3-MPTMS: 3] | 0.5 [PEMA] | 0.2 [Colloidal Silica] | 14.5 [Bis-MEPP: 33; UDMA: 38; TEGDMA: 29] | 161 | 6.8 | 40 | 5.9 | Good for core construction |
| Example 33 | 5.0 [G1: 55/THFTC: 45/ TEOS: 3; 3-MPTMS: 2] | 0.5 [PEMA] | 0.2 [Colloidal Silica] 56.3 [G2] | 36.2 [UDMA: 33; TEGDMA: 38; 2-HEMA: 29] | 117 | 1.9 | 17 | 6.2 | Good as a sealing material for pit and fissure |
| Example 34 | 22 [G2: 90/Tart: 10/ TEOS: 3; 3-MPTMS: 3] | 0.4 [PEMA] | 37.4 [G2: 100; TEOS: 15; 3-MPTMS: 3] | 40.2 [Bis-MEPP: 33; UDMA: 38; TEGDMA: 29] | 149 | 0.2 | 69 | 6.0 | Good as a sealing material for pit and fissure |
| Example 35 | 75.8 [G2: 65/Tart: 35/ TEOS: 50; 3-MPTMS: 15] | 1 [PMMA] | 0.2 [Colloidal Silica] | 23 [Bis-MEPP: 33; UDMA: 38; TEGDMA: 29] | 141 | 0.3 | 39 | 5.9 | Good as a filling restorative |
| Comparison Example 1 | 77 [G2: 100/3-MPTMS: 2] | 0.8 [PEMA] | 0.2 [Colloidal Silica] | 22 [Bis-MEPP: 33; UDMA: 38; TEGDMA: 29] | 149 | 0.2 | Less than the detection limit | 6.2 | No fluorine ion was released. |
| Comparison Example 2 | 2.3 [G2: 90/Tart: 10/3-MPTMS: 3] | 0.8 [PEMA] | 76.1 [G2: 100; 3-MPTMS: 4] | 20.8 [Bis-MEPP: 20; UDMA: 46; 2-HEMA: 34] | 150 | 33 | 0.3 | 5.9 | A fluorine ion was less released. |
| Comparison Example 3 | 76 [G2: 52/Tart: 48/ TEOS: 3; 3-MPTMS: 3] | 1 [PEMA] | | 23 [Bis-MEPP: 20; UDMA: 46; 2-HEMA: 34] | 98 | 8.6 | 71 | 1.1 | The pH was low. |
| Comparison Example 4 | 76 [G2: 99.96/Tart: 0.04/ TEOS: 3; 3-MPTMS: 3] | 0.8 [PEMA] | 0.2 [Colloidal Silica] | 23 [Bis-MEPP: 20; UDMA: 46; 2-HEMA: 34] | 152 | 0.2 | 0.05 | 6.2 | A fluorine ion was less released. |
| Comparison Example 5 | 76 [G1: 96/Tart: 4/TEOS: 3; 3-MPTMS: 3] | 0.04 [PMMA] | 0.2 [Colloidal Silica] | 23.76 [Bis-MEPP: 20; UDMA: 46; 2-HEMA: 34] | 157 | 0.2 | 33 | 5.8 | The resin composition was sticky and poor in workability |
| Comparison Example 6 | 52 [G1: 96/Tart: 4/TEOS: 3; 3-MPTMS: 3] | 23 [PMMA] | | 25 [Bis-MEPP: 20; UDMA: 46; 2-HEMA: 34] | 65 | 0.6 | 27 | 6.1 | The resin composition was poor in mechanical characteristics |
| Comparison Example 7 | Commercially available composite resin [a trade name: Herculite XRV, made by Kurr Corp. | | | | 132 | 0.2 | Less than the detection limit | 6.2 | No fluorine ion was released |

TABLE 1-continued

| | Reaction Product (weight %) [Glass powder (parts by weight)/Organic Acid/Alkoxy Compound] | Polymer (weight %) | Filler (weight %) [Kind of Filler (parts by weight)] | Monomer (weight %) [Kind of Monomer (parts by weight)] | Bending Strength (MPa) | Surface Roughness ($\mu m$) | Fluorine Ion ($\mu g/cm^2$) | pH | Remarks |
|---|---|---|---|---|---|---|---|---|---|
| Comparison Example 8 | Commercially available composite resin [a trade name: Graft LC II, made by GC Corp] | | | | 150 | 3.9 | Less than the detection limit | 6.2 | No fluorine ion was released. |
| Comparison Example 9 | Commercially available resin-reinforced glass ionomer cement [a trade name: Fuji II LC, made by GC Corp.] | | | | 61 | 3.9 | 66 | 5.8 | Kneading of powder and liquid was required. |
| Comparison Example 10 | Commercially available compomer composite resin [a trade name: Dyract, made by Dentz Ply Corp.] | | | | 100 | 1.4 | 24 | 4.7 | The resin composition was insufficient in both mechanical characteristics and ability for releasing a fluorine ion. |

The abbreviations in Table 1 are as follows.
(Organic Acid)
L-AS: L-Aspartic acid
L-Ag: L-Arginine
Citr: Citric acid
GN: Glycine
GOL: Glycolic acid
DL-G: DL-Glyceric acid
GLC: Gluconic acid
GlcUA: Glucuronic acid
GLT: Glutaric acid
AdC: Acetonedicarboxylic acid
Tart: Tartaric acid
cptC: Cyclopentanetetracarboxylic acid
dGL: Diglycolic acid
dEtM: Diethylmalonic acid
L-Cys: L-Cysteic acid
Ox: Oxalic acid
SuSA: Sulfosalicylic acid
TTR: Tartronic acid
TCAR: Tricarballylic acid
THFTC: Tetrahydrofurantetracarboxylic acid
mBTC: meso-Butane-1,2,3,4-tetracarboxylic acid
TMRT: Trimellitic acid
Lac: Lactic acid
MLN: Malonic acid
DL-M: DL-Mandelic acid
BzC6: Benzenehexacarboxylic acid
Mal: Malic acid
(Alkoxy Compound)
TEOS: Tetraethoxysilane
3-MPTMS: 3-Methacryloxypropyl trimethoxysilane
3-APTMS: 3-Aminopropyl trimethoxysilane
(Monomer)
2-HEMA: 2-Hydroxyethyl methacrylate
3-HPMA: 3-Hydroxypropyl methacrylate
2-HPMA: 2-Hydroxypropyl methacrylate
GMA: Glycidyl methacrylate
Bis-2OHMOPP: 2,2-Bis[4-(2-hydroxy-3-methacryloxypropoxy)phenyl]propane
Bis-MEPP: 2,2-Bis(4-methacryloxypolyethoxyphenyl) propane
TEGDMA: Triethylene glycol dimethacrylate
BG: 1,3-Butanediol dimethacrylate
UDMA: Di-2-methacryloxyethyl-2,2,4-trimethylhexamethylene dicarbamate
2-OHDMP: 2-Hydroxy-1,3-dimethacryloxypropane
(Polymer)
PMMA: Polymethyl methacrylate
PEMA: Polyethyl methacrylate
PMEA: 2-hydroxyethyl methacrylate-methyl methacrylate copolymer
PStMA: Styrene-maleic anhydride copolymer As is clear from the results as shown in Table 1, the dental filling resin composition according to the present invention is superior in mechanical characteristics such as bending strength or surface smoothness, has an ability to release a fluorine ion, is superior in workability and esthetics, and has X-ray contrast properties. That is, the dental filling resin composition according to the present invention effectively possesses superior characteristics as both of a dental composite resin and a dental glass ionomer in combination and therefore, can be suitably used for a wide variety of clinical applications such as filling restoration of tooth, core construction, or sealing of pit and fissure and should greatly contribute to the field of dental therapy.

While the invention has been described in detail and with reference to specific embodiments thereof, it will be apparent to one skilled in the art that various changes and modifications can be made therein without departing from the spirit and scope thereof.

What is claimed is:

1. A dental filling resin composition comprising:
   (A) a reaction product between an aluminosilicate glass powder containing at least one element selected from Ca, Sr, and Ra and an organic acid containing one or more carboxyl groups in one molecule thereof,
   (B) a methanol-insoluble polymer,
   (C) a monomer containing at least one unsaturated double bond and having no acidic group, and
   (D) a polymerization initiator,
   wherein said organic acid containing one or more carboxyl groups in one molecule thereof is one or two or more members selected from L-aspartic acid, L-arginine, citric acid, glycine, glycolic acid, DL-glyceric acid, gluconic acid, glucuronic acid, glutaric acid, acetonedicarboxylic acid, tartaric acid, cyclopentanetetracarboxylic acid, diglycolic acid, diethylmalonic acid, L-cysteic acid, oxalic acid, sulfosalicylic acid, tartronic acid, tricarballylic acid, tetrahydrofurantetracarboxylic acid, meso-butane-1,2,3,4-tetracarboxylic acid, trimellitic acid, lactic acid, benzenepentacarboxylic acid, malonic acid, DL-mandelic acid, benzenehexacarboxylic acid, and malic acid and is reacted in an amount of from 0.1 to 45% by weight of said reaction product.

2. A dental filling resin composition as claimed in claim 1, wherein said aluminosilicate glass powder containing at least one element selected from Ca, Sr, and Ra is a fluoroaluminosilicate glass powder comprising from 20 to 50% by weight of $SiO_2$, from 20 to 40% by weight of $Al_2O_3$, from 15 to 40% by weight of SrO, from 1 to 20% by weight of $F_2$, and from 0 to 15% by weight of $P_2O_5$ in terms of reduced amounts and not substantially containing Li, Na, K, Rb, Cs, Be, Mg, and Ba.

3. A dental filling resin composition as claimed in any one of claims 1 to 2, wherein said methanol-insoluble polymer is one or two or more members selected from pearl polymerization powder, ground powder of bulk polymer, and powder of emulsion polymer and is contained in an amount of from 0.1 to 20% by weight in said dental filling resin composition.

4. A dental filling resin composition as claimed in any one of claims 1 to 2, wherein said polymerization initiator is a photopolymerization initiator comprising a sensitizer and a reducing agent, which causes a polymerization reaction upon irradiation with a light, or a chemical polymerization initiator which causes a polymerization reaction by a redox reaction.

5. A dental filling resin composition as claimed in any one of claims 1 to 2, wherein said reaction product is a reaction product prepared by aging a mixture of a slurry of said aluminosilicate glass powder containing at least one element selected from Ca, Sr, and Ra suspended in an organic solvent and an aqueous solution of said organic acid containing one or more carboxyl groups in one molecule thereof at room temperature and then heating for drying and is contained in an amount of from 5 to 85% by weight in said dental filling resin composition.

6. A dental filling resin composition as claimed in any one of claims 1 to 2, wherein said reaction product is modified with an alkoxy compound.

7. A dental filling resin composition as claimed in any one of claims 1 to 2, further comprising (E) a filler comprising one or two or more members selected from colloidal silica, barium glass powder, and aluminosilicate glass powder containing at least one element selected from Ca, Sr, and Ra.

8. A dental filling resin composition as claimed in claim 7, wherein said filler is modified with an alkoxy compound.

9. A method of making a dental filling resin composition, comprising mixing (A) a reaction product between an aluminosilicate glass powder containing at least one element selected from Ca, Sr, and Ra and an organic acid containing one or more carboxyl groups in one molecule thereof, (B) a methanol-insoluble polymer, (C) a monomer containing at least one unsaturated double bond and having no acidic group, and (D) a polymerization initiator, wherein said organic acid containing one or more carboxyl groups in one molecule thereof is one or two or more members selected from L-aspartic acid, L-arginine, citric acid, glycine, glycolic acid, DL-glyceric acid, gluconic acid, glucuronic acid, glutaric acid, acetonedicarboxylic acid, tartaric acid, cyclopentanetetracarboxylic acid, diglycolic acid, diethylmalonic acid, L-cysteic acid, oxalic acid, sulfosalicylic acid, tartronic acid, tricarballylic acid, tetrahydrofurantetracarboxylic acid, meso-butane-1,2,3,4-tetracarboxylic acid, trimellitic acid, lactic acid, benzenepentacarboxylic acid, malonic acid, DL-mandelic acid, benzenehexacarboxylic acid, and malic acid and is reacted in an amount of from 0.1 to 45% by weight of said reaction product.

10. The method of claim 9, wherein said aluminosilicate glass powder containing at least one element selected from Ca, Sr, and Ra is a fluoroaluminosilicate glass powder comprising from 20 to 50% by weight of $SiO_2$, from 20 to 40% by weight of $Al_2O_3$, from 15 to 40% by weight of SrO, from 1 to 20% by weight of $F_2$, and from 0 to 15% by weight of $P_2O_5$ in terms of reduced amounts and not substantially containing Li, Na, K, Rb, Cs, Be, Mg, and Ba.

11. The method of claim 9, further comprising mixing (E) a filler comprising one or two or more members selected from colloidal silica, barium glass powder, and aluminosilicate glass powder containing at least one element selected from Ca, Sr, and Ra.

12. The dental filling resin composition prepared by the process of claim 9.

13. The dental filling resin composition prepared by the process of claim 11.

* * * * *